United States Patent
Lee et al.

(10) Patent No.: US 10,983,105 B2
(45) Date of Patent: Apr. 20, 2021

(54) ROTATING APPARATUS AND METHOD FOR MEASURING ACID-ROCK REACTION CHARACTERISTICS IN HIGH TEMPERATURE AND PRESSURE

(71) Applicant: INDUSTRY FOUNDATION OF CHONNAM NATIONAL UNIVERSITY, Gwangju (KR)

(72) Inventors: Jeonghwan Lee, Gwangju (KR); Hyunsang Yoo, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 241 days.

(21) Appl. No.: 15/928,568

(22) Filed: Mar. 22, 2018

(65) Prior Publication Data
US 2018/0275112 A1    Sep. 27, 2018

(30) Foreign Application Priority Data
Mar. 23, 2017 (KR) .......................... 10-2017-0036580

(51) Int. Cl.
*G01N 33/24*    (2006.01)
*G01N 25/48*    (2006.01)
(Continued)

(52) U.S. Cl.
CPC ............... *G01N 33/24* (2013.01); *B01J 3/00* (2013.01); *B01J 19/0006* (2013.01); *B01J 19/18* (2013.01);
(Continued)

(58) Field of Classification Search
CPC .. G01N 33/24; G01N 25/4846; G01N 25/486; G01N 2033/243; G01N 13/00;
(Continued)

(56) References Cited

U.S. PATENT DOCUMENTS

| | | | | |
|---|---|---|---|---|
| 4,093,544 A | * | 6/1978 | Ross | C01C 1/10 95/158 |
| 5,387,273 A | * | 2/1995 | Hartman | C22B 15/0015 75/401 |
| 2014/0057356 A1 | * | 2/2014 | Qiu | E21B 43/16 436/34 |

OTHER PUBLICATIONS

Core Laboratories et al. (Rotating Disc Acid Reaction System, CRS-100, https://web.archive.org/web/20141223230121/https://www.corelab.com/cli/drilling-and-stimulation/rotating-disc-acid-reaction-system, 2014 (Year: 2014).*

(Continued)

*Primary Examiner* — Benjamin R Whatley
*Assistant Examiner* — Jean Caraballo-Leon
(74) *Attorney, Agent, or Firm* — Sughrue Mion, PLLC

(57) ABSTRACT

An apparatus for controlling acid-rock reaction includes a first reactor, a second reactor connected to the first reactor and configured to produce a spent acid through reaction of a rock with an acid aqueous solution and to introduce the spent acid into the first reactor, the first reactor being configured to react a rock disk with the spent acid introduced from the second reactor, a sample extractor connected to the first reactor and configured to extract, from the first reactor, a predetermined amount of the spent acid reacting with the rock disk in the first reactor, and a data acquisition device configured to acquire temperature and pressure data of the first reactor and the second reactor and control the first reactor and the second reactor based on he acquired temperature and pressure data of the first reactor and the second reactor.

11 Claims, 2 Drawing Sheets

(51) Int. Cl.
  *B01L 3/00*   (2006.01)
  *B01J 19/18*  (2006.01)
  *B01J 19/00*  (2006.01)
  *B01J 3/00*   (2006.01)

(52) U.S. Cl.
  CPC .......... *B01L 3/508* (2013.01); *G01N 25/4846* (2013.01); *B01J 2219/00177* (2013.01); *B01L 2300/0663* (2013.01); *G01N 25/486* (2013.01); *G01N 2033/243* (2013.01)

(58) Field of Classification Search
  CPC . G01N 2013/003; B01J 19/18; B01J 19/0006; B01J 3/00; B01J 2219/00177; B01L 3/508; B01L 2300/0663
  See application file for complete search history.

(56) References Cited

OTHER PUBLICATIONS

Grace Instruments et al. (M9400 Automatic Rotating Disc Acid Reactor, https://web.archive.org/web/20151228102435/https://www.graceinstrument.com/M9400.php, 2015 (Year: 2015).*

M.H. Al-Khaldi et al., "Reaction of citric acid with calcite", Chemical Engineering Science, 2007, pp. 5880-5896, vol. 62.

Office Action for corresponding KR 10-2017-0036580, dated Apr. 20, 2017.

* cited by examiner

ROTATING APPARATUS AND METHOD FOR MEASURING ACID-ROCK REACTION CHARACTERISTICS IN HIGH TEMPERATURE AND PRESSURE

CROSS-REFERENCE TO RELATED APPLICATION(S) AND CLAIM OF PRIORITY

The present application claims the benefit under 35 U.S.C. § 119(a) to a Korean patent application filed in the Korean Intellectual Property Office on Mar. 23, 2017, and assigned Serial No. 10-2017-0036580, the entire disclosure of which is hereby incorporated by reference.

TECHNICAL FIELD OF THE INVENTION

The present disclosure relates generally to technology for measuring reaction characteristics, and more particularly, to an apparatus and a method for measuring reaction characteristics through an acid-rock rotating reaction in high temperature and pressure.

BACKGROUND OF THE INVENTION

The global distribution of carbonate reservoirs is estimated to exceed the 60% of oil and 40% of gas reserves in the world, and in particular, more than 70% of the oil reservoirs in the Middle East are held in carbonate reservoirs. However, it is known that the carbonate reservoirs are difficult to be characterized due to the heterogeneous nature and complexity of geo-tectonics, and also, if such difficulty is not considered in the field, reliability and effect of stimulation techniques might be degraded.

In general, matrix acidizing from among various stimulation techniques is widely used in order to enhance oil recovery of a carbonate reservoir. The matrix acidizing refers to a method that enhances productivity by injecting an acid into a reservoir and creating highly conductive channels that are known as wormholes. The success of the matrix acidizing depends on a shape of the wormhole such as length, diameter, distribution, etc., and the shape of the wormhole may depend on acid-rock reaction characteristics. In this case, a dissolution rate and a diffusion coefficient are used as very important parameters to analyze acid-rock reaction characteristics.

In order to decide an appropriate injection condition when designing an acidizing process for a specific target reservoir in future, analysis of acid-rock reaction characteristics should be performed to enhance the efficiency of acidizing.

However, the commercial apparatuses do not consider high temperature and pressure as experimental conditions to practically implement a flow of an acid in a reservoir, and as the wormhole extends deeper into the formation, the front of the wormhole is further reacted with spent acid, which is a partially reacted acid with reaction products such as calcium and magnesium ions during the acid-rock reaction. Therefore, there is a demand for development of an apparatus for measuring acid-rock reaction characteristics considering an effect of a spent acid in the reservoir condition.

SUMMARY OF THE INVENTION

To address the above-discussed deficiencies of the prior art, it is a primary aspect of the present disclosure to provide an apparatus and a method for measuring acid-rock reaction characteristics, which can measure a dissolution rate and a diffusion coefficient through an acid-rock reaction experiment in a high temperature and pressure reservoir condition, as a solution to set an acid injecting condition which is specialized for a specific target reservoir and is more effective in designing acidizing in a carbonate reservoir, and can implement an acidizing system by considering an effect of a spent acid.

According to an embodiment of the present disclosure to achieve the above-described object, an apparatus for measuring acid-rock reaction characteristics includes: a first reactor configured to make a reaction of a rock disk with an acid; a second reactor configured to produce a spent acid through reaction of a rock with an acid aqueous solution, and to introduce the spent acid into the first reactor; and a sample extractor configured to extract a predetermined amount of acid reacting with the rock disk in the first reactor.

In addition, the first reactor may be configured to make a reaction of the rock disk with the acid in a high temperature and pressure as reservoir condition.

In addition, the second reactor may be configured to produce the spent acid by reacting the rock with the acid aqueous solution in the high temperature and pressure as reservoir condition.

In addition, the first reactor may include: a first reaction vessel in which the rock disk reacts with the acid; a first heating jacket configured to maintain a temperature of the first reaction vessel in the reservoir condition; a first magnetic drive configured to rotate the rock disk when the rock disk reacts with the acid; and a first sensor configured to measure internal temperature and pressure of the first reaction vessel.

In addition, the second reactor may include: a second reaction vessel configured to store the spent acid produced through the reaction of the rock with the acid aqueous solution in the reservoir condition; a second heating jacket configured to maintain a temperature of the second reaction vessel in the reservoir condition; a second magnetic drive configured to rotate a permeable container containing the rock when the rock reacts with the acid aqueous solution; a second sensor configured to measure internal temperature and pressure of the second reaction vessel; and a cylinder configured to introduce the spent acid stored in the second reaction vessel into the first reactor by pushing the spent acid to the outside of the second reaction vessel.

In addition, the apparatus according to an embodiment of the present disclosure may further include a data acquisition device configured to acquire temperature and pressure data of the first reactor and the second reactor from the first sensor and the second sensor, and to adjust the temperatures of the first reaction vessel and the second reaction vessel by controlling the first heating jacket and the second heating jacket.

In addition, the data acquisition device may be configured to adjust rotating speeds of the first magnetic drive and the second magnetic drive.

In addition, the sample extractor may include: a sampling line configured to have a predetermined amount of acid loaded therein; a sampling tank configured to store an acid; a first sampling valve configured to move the acid reacting with the rock disk in the first reactor to the sampling line; and a second sampling valve configured to move the acid loaded in the sampling line to the sampling tank.

In addition, the sampling tank may be configured to make it easy to acquire a sample by storing an acid and reducing pressure prior to acquiring a sample during an experiment in high pressure.

In addition, the apparatus according to an embodiment of the present disclosure may further include a vent configured to discharge internal fluid to the outside after the reaction finishes in the first reactor and the second reactor.

In addition, the vent may include: a neutralization tank configured to load a neutralizing agent therein to neutralize an acid; a first vent valve configured to move internal fluid of the first rector to the neutralization tank after the reaction finishes; and a second vent valve configured to move internal fluid of the second reactor to the neutralization tank after the reaction finishes.

In addition, the acid extracted by the sample extractor may be used to calculate a dissolution rate and a diffusion coefficient of the acid reacting with the rock through the first reactor and the second reactor.

In addition, the acid reacting with the rock disk may be at least one acid selected from the group consisting of a hydrochloric acid, an organic acid, and an acid blend, and the rock may include a rock which has reactivity with an acid, and the rock may include a carbonate rock.

According to another embodiment of the present disclosure, a method for measuring acid-rock reaction characteristics includes the steps of: producing a spent acid by reacting a rock with an acid aqueous solution, and introducing the spent acid into a first reactor; reacting a rock disk with an acid in the first reactor; and extracting a predetermined amount of acid reacting with the rock disk in the first reactor.

According to embodiments of the present disclosure described above, a dissolution rate and a diffusion coefficient can be more exactly measured by rotating the rock disk in an acid at high temperature and pressure in consideration of the reaction characteristics of the rock dissolved in the acid, and then obtaining a predetermined amount of acid reacting the rock with time.

In addition, according to embodiments of the present disclosure, a flow of an acid in a real reservoir can be implemented by producing a spent acid of the reservoir condition and then reacting the rock disk with the spent acid in the single apparatus.

Other aspects, advantages, and salient features of the invention will become apparent to those skilled in the art from the following detailed description, which, taken in conjunction with the annexed drawings, discloses exemplary embodiments of the invention.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION OF THE INVENTION

The present disclosure will be described in more detail with reference to the accompanying drawings.

Figure 1:
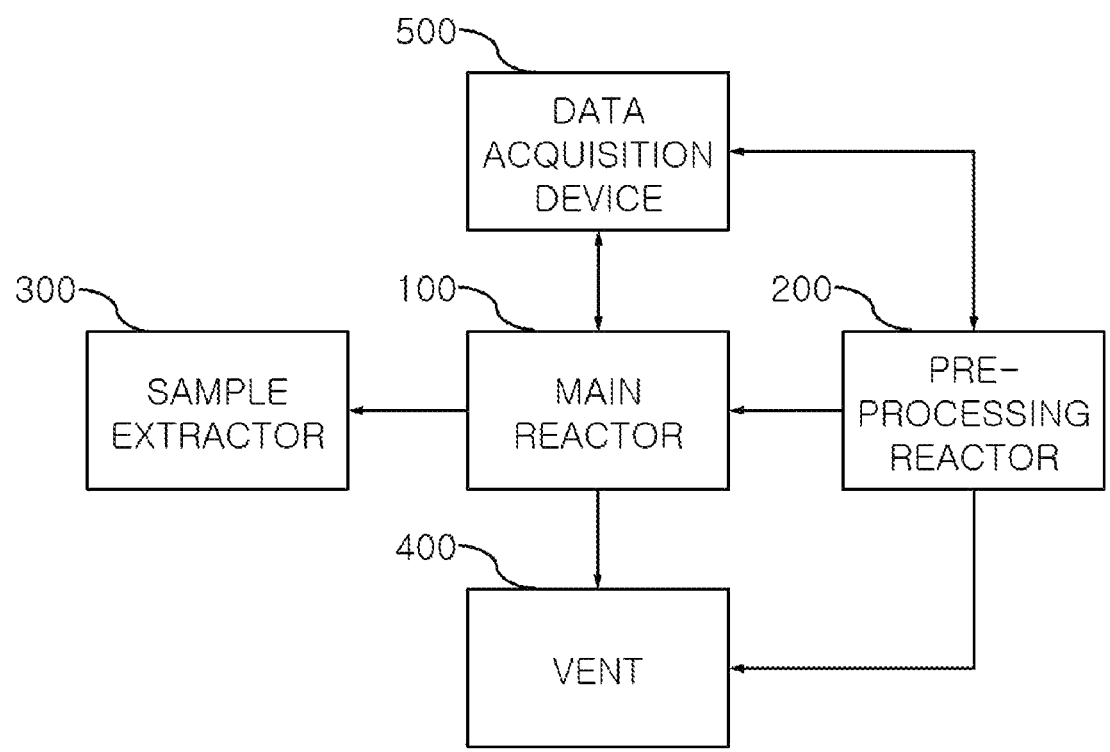
FIG. 1 is a view showing a configuration of a rotating apparatus for measuring acid-rock reaction characteristics according to an embodiment of the present disclosure.

FIG. 1 is a view showing a configuration of a rotating apparatus for measuring acid-rock reaction characteristics according to an embodiment of the present disclosure.

The rotating apparatus for measuring the acid-rock reaction characteristics according to an embodiment of the present disclosure measures a dissolution rate, a diffusion coefficient, and an order of reaction of a rock having a property of dissolving in an acid through an acid-rock rotating reaction in high temperature and pressure.

In addition, the rotating apparatus for measuring the acid-rock reaction characteristics according to an embodiment of the present disclosure refers to an apparatus for measuring a dissolving ability of an acid and for analyzing reaction characteristics with a rock after producing a spent acid (an acid having already induced a reaction).

The rotating apparatus for measuring the acid-rock reaction characteristics according to an embodiment of the present disclosure includes a main reactor 100, a pre-processing reactor 200, a sample extractor 300, a vent 400, and a data acquisition device 500 as shown in FIG. 1.

The main reactor 100 makes a reaction of a rock disk, which is a reaction target and is fixed to a shaft of magnetic drive, with an acid in a high temperature and pressure condition. The main reactor 100 and the pre-processing reactor 200 may be connected with each other via a pipeline.

The pre-processing reactor 200 produces a spent acid by reacting a rock and an acid aqueous solution with each other in a high temperature and pressure as reservoir condition, and stores the spent acid.

The sample extractor 300 extracts a predetermined amount of acid reacting with the rock in the main reactor 100.

The data acquisition device 500 controls reaction vessel temperatures of the reactors 100 and 200 and a rotation speed of the magnetic drive, based on pressure and temperature of the main reactor 100 and the pre-processing reactor 200.

The main reactor 100 and the pre-processing reactor 200 are connected with the vent 400. The vent 400 discharges internal fluid of the apparatus to the outside after the experiment finishes.

Figure 2:
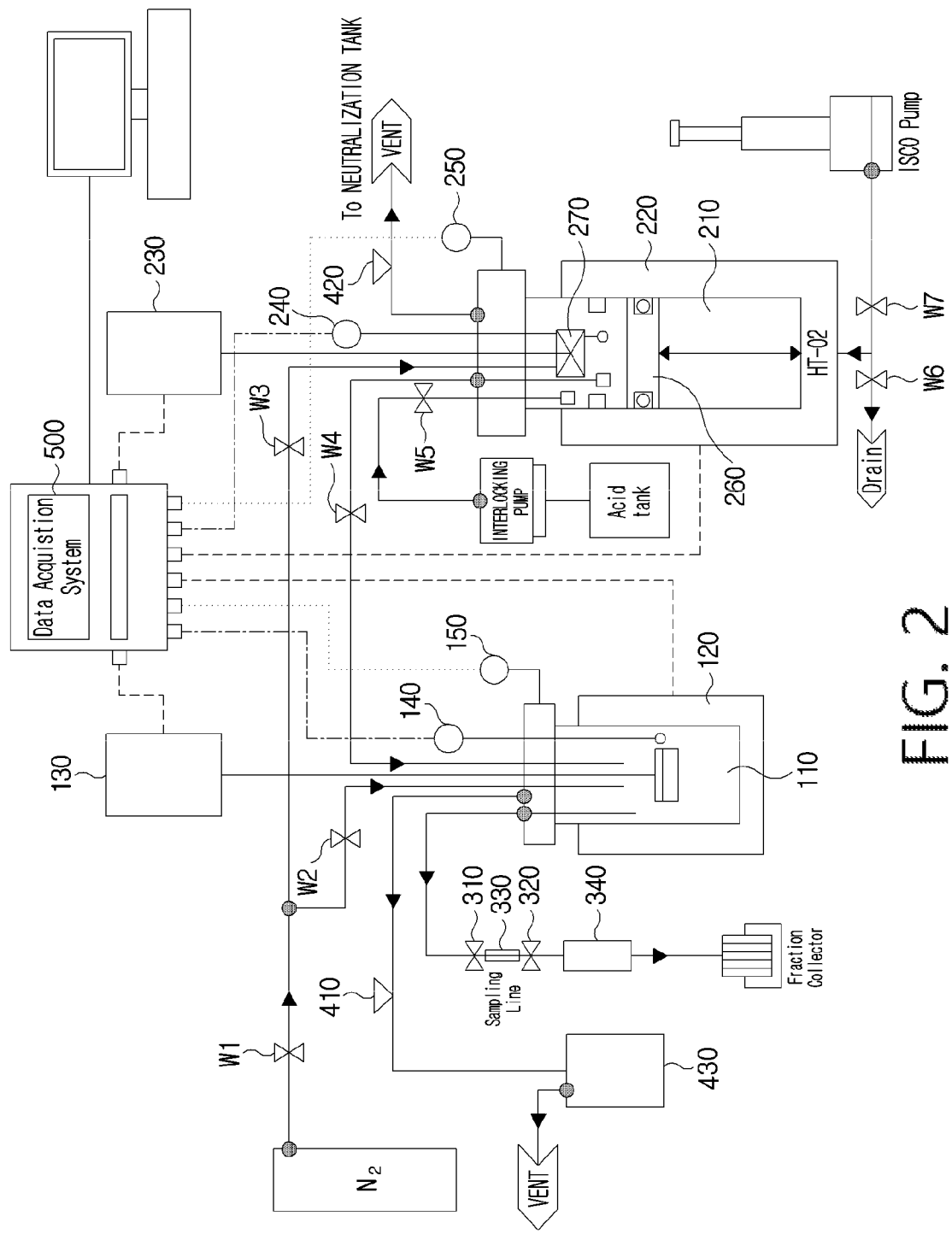
FIG. 2 is a detailed diagram of the rotating apparatus for measuring the acid-rock reaction characteristics shown in FIG. 1.

Hereinafter, the rotating apparatus for measuring the acid-rock reaction characteristics according to an embodiment of the present disclosure will be described in detail with reference to FIG. 2. FIG. 2 is a detailed diagram of the rotating apparatus for measuring the acid-rock reaction characteristics of FIG. 1.

The main reactor 100 which makes a reaction of the rock disk with the acid includes a main reaction vessel 110, a first heating jacket 120, a first magnetic drive 130, a first temperature sensor 140, and a first pressure sensor 150.

The main reaction vessel 110 is a vessel in which the rock and the acid react with each other, and the first heating jacket 120 is installed to surround the main reaction vessel 110 to set and maintain the temperature of the main reaction vessel 110 according to the reservoir condition.

The first magnetic drive 130 is a portion that has the rock disk fixed at an end of the shaft connected therewith, and where the fixed rock disk reacts with the acid, and constantly maintains a reaction area between the rock and the acid by rotating the rock disk at a predetermined speed.

The rock disk, which is a reaction target, may be a carbonate rock, and does not exclude other rocks having reactivity with an acid. In addition, the acid reacting with the rock disk may be at least one acid selected from the group consisting of an hydrochloric acid, an organic acid, and an acid blend, and does not exclude other acids.

The first temperature sensor 140 and the first pressure sensor 150 may identify whether the temperature and pressure of the main reaction vessel 110 are maintained in the reservoir condition by measuring the internal temperature and pressure of the main reaction vessel 110.

The pre-processing reactor 200 which produces the spent acid by reacting the rock with the acid includes a pre-processing reaction vessel 210, a second heating jacket 220, a second magnetic drive 230, a second temperature sensor 240, a second pressure sensor 250, a cylinder 260, and a permeable container 270.

The pre-processing reaction vessel 210 is a vessel that stores the spent acid which is produced through the reaction of the rock and the acid aqueous solution in the reservoir condition, and the second heating jacket 220 is installed to surround the pre-processing reaction vessel 210 and to maintain the temperature of the pre-processing reaction vessel 210 in the reservoir condition.

The second magnetic drive 230 may have the rock for producing a spent acid positioned in the permeable container 270 disposed at an end of the shaft connected therewith, and may rotate the permeable container 270 at a regular speed when the acid and the rock react with each other.

The rock which is a target for producing the spent acid may be a carbonate rock, and does not exclude other rocks having reactivity.

The second temperature sensor 240 and the second pressure sensor 250 may measure internal temperature and pressure of the pre-processing reaction vessel 210, thereby identifying whether the temperature and pressure of the pre-processing reaction vessel 210 are maintained in the reservoir condition.

In addition, the cylinder 260 pushes the spent acid stored in the pre-processing reaction vessel 210 to the outside, thereby introducing the spent acid into the main reactor 100.

The sample extractor 300 which extracts a predetermined amount of acid reacting with the rock in the main reactor 100 includes a first sampling valve 310, a second sampling valve 320, a sampling line 330, and a sampling tank 340.

The first sampling valve 310 serves to move the acid reacting with the rock disk in the main reactor 100 to the sampling line 330. The sampling line 330 may be fabricated to hold a fluid of 10 ml.

The second sampling valve 320 enables the acid loaded in the sampling line 330 to move to the sampling tank 340, such that a predetermined amount of sample can be obtained. The sampling tank 340 serves to store the acid before a sample is obtained at an experiment conducted under high pressure, and enables a sample to be obtained by reducing the pressure.

The vent 400, which discharges internal fluid generated in the apparatus to the outside after the reaction of the rock with the acid finishes, includes a first vent valve 410, a second vent valve 420, and a neutralization tank 430.

The first vent valve 410 may introduce the fluid introduced into the main reactor 100 and the fluid generated through the reaction of the acid and the rock into the neutralization tank 430 of the vent 400.

The second vent valve 420 may introduce the fluid introduced from the pre-processing reactor 200 and the fluid generated by producing the spent acid into the neutralization tank 430 of the vent 400.

The neutralization tank 430 may load a sodium hydroxide aqueous solution therein as a neutralizing agent to neutralize the acid, and may neutralize the fluid introduced from the main reactor 100 and the pre-processing reactor 200, and then discharge the fluid to the outside of the apparatus.

The data acquisition device 500 may acquire temperature and pressure data of the main reactor 100 and the pre-processing reactor 200 measured by the first temperature sensor 140 and the first pressure sensor 150 of the main reactor 100 and the second temperature sensor 240 and the second pressure sensor 250 of the pre-processing reactor 200, and may adjust the temperatures of the main reactor 100 and the pre-processing reactor 200 by controlling the first heating jacket 120 and the second heating jacket 220 based on the acquired temperature and pressure data.

In addition, the data acquisition device 500 may adjust the rotating speed of the first magnetic drive 130 for rotating the shaft at which the rock disk, which is a reaction target, is fixed in the main reactor 100, and the rotating speed of the second magnetic drive 230 for rotating the shaft to which the permeable container 270 for producing the spent acid is connected in the pre-processing reactor 200.

Up to now, the rotating apparatus and method for measuring the acid-rock reaction characteristics in high temperature and pressure have been described with reference to preferred embodiments.

The apparatus and THE method for measuring the acid-rock reaction characteristics according to an embodiment of the present disclosure produce the spent acid at the reservoir condition and then reacts the rock disk with the spent acid in the single apparatus, such that a more practical flow of an acid can be implemented in a reservoir.

In particular, a dissolution rate and a diffusion coefficient can be more exactly measured by rotating the rock disk in an acid at high temperature and pressure in consideration of the reaction characteristics of the rock dissolved in the acid, and then obtaining a predetermined amount of acid reacting the rock with time, and a flow of an acid in a real reservoir can be implemented by producing a spent acid of the reservoir condition and then reacting the rock disk with the spent acid in the single apparatus.

In addition, while preferred embodiments of the present disclosure have been illustrated and described, the present disclosure is not limited to the above-described specific embodiments. Various changes can be made by a person skilled in the art without departing from the scope of the present disclosure claimed in claims, and also, changed embodiments should not be understood as being separate from the technical idea or prospect of the present disclosure.

What is claimed is:

1. An apparatus for controlling acid-rock reactions, the apparatus comprising:
a first reactor;
a second reactor connected to the first reactor and configured to produce a spent acid through reaction of a rock with an acid aqueous solution, and to introduce the spent acid into the first reactor, wherein the first reactor is configured to react a rock disk with the spent acid introduced from the second reactor;

a sample extractor connected to the first reactor and configured to extract, from the first reactor, a predetermined amount of the spent acid reacting with the rock disk in the first reactor; and a data acquisition device configured to acquire temperature and pressure data of the first reactor and the second reactor and control the first reactor and the second reactor based on he acquired temperature and pressure data of the first reactor and the second reactor, wherein the first reactor is configured to react the rock disk with the spent acid under a first reservoir condition comprising a first high temperature and a first high pressure, wherein the second reactor is configured to produce the spent acid by reacting the rock with the acid aqueous solution under a second reservoir condition comprising a second high temperature and a second high pressure, wherein the first reactor comprises:
a first reaction vessel in which the rock disk reacts with the spent acid;
a first heating jacket configured to maintain the temperature of the first reservoir condition in the first reaction vessel;
a first magnetic drive configured to rotate a shaft connected to the rock disk at a first rotating speed when the rock disk reacts with the spent acid; and
a first sensor configured to measure an internal temperature and a pressure of the first reaction vessel, wherein the second reactor comprises:
a second reaction vessel configured to include a permeable container to contain the rock and further configured to store the spent acid produced through the reaction of the rock with the acid aqueous solution under the second reservoir condition;
a second heating jacket configured to maintain the temperature of the second reservoir condition in the second reaction vessel;
a second magnetic drive configured to rotate a shaft connected to the permeable container containing the rock at a second rotating speed when the rock reacts with the acid aqueous solution;
a second sensor configured to measure an internal temperature and a pressure of the second reaction vessel; and
a cylinder configured to introduce the spent acid stored in the second reaction vessel into the first reactor by pushing the spent acid to the outside of the second reaction vessel, wherein the data acquisition device is further configured to acquire the temperature and pressure data of the first reactor and the second reactor from the first sensor and the second sensor and to adjust temperatures of the first reaction vessel and the second reaction vessel by controlling the first heating jacket and the second heating jacket, and wherein the data acquisition device is configured to adjust the first rotating speed of the first magnetic drive and the second rotating speed of the second magnetic drive based on the acquired temperature and pressure data of the first reactor and the second reactor.

2. The apparatus of claim 1, wherein the sample extractor comprises a first sampling valve, a sampling line connected to the first sampling valve, a second sampling valve connected to the sampling line, and a sampling tank connected to the second sampling valve, wherein the first sampling valve is configured to move the acid reacting with the rock disk in the first reactor to the sampling line, the sampling line is configured to have the acid moved from the first reactor loaded therein, the second sampling valve is configured to move the acid loaded in the sampling line to the sampling tank, and the sampling tank is configured to store the acid moved from the sampling line.

3. The apparatus of claim 1, further comprising a vent connected to the first reactor and the second reactor and configured to discharge internal fluid of the first reactor to the outside after the reaction of the rock disk with the acid finishes in the first reactor and discharge internal fluid of the second reactor to the outside after the reaction of the rock with the acid aqueous solution finishes in the second reactor.

4. The apparatus of claim 3, wherein the vent comprises:
a neutralization tank configured to load a neutralizing agent therein to neutralize an acid;
a first vent valve configured to move the internal fluid of the first reactor to the neutralization tank after the reaction of the rock disk with the acid finishes; and
a second vent valve configured to move the internal fluid of the second reactor to the neutralization tank after the reaction of the rock with the acid aqueous solution finishes.

5. The apparatus of claim 1, wherein the acid extracted by the sample extractor is used to calculate a dissolution rate and a diffusion coefficient of the acid reacting with the rock through the first reactor and the second reactor.

6. The apparatus of claim 1, wherein the first reactor includes the rock disk and the spent acid, and the spent acid reacting with the rock disk is at least one acid selected from the group consisting of a hydrochloric acid, an organic acid, and an acid blend, and wherein the second reactor includes the rock, and the rock comprises a carbonate rock.

7. A method for controlling acid-rock reactions by an apparatus including a first reactor, a second reactor, a sample extractor, and a data acquisition device, the method comprising the steps of:

producing a spent acid by reacting a rock with an acid aqueous solution in the second reactor, and introducing the spent acid into a first reactor;

reacting a rock disk with the spent acid introduced from the second reactor in the first reactor;

extracting, by the sample extractor, from the first reactor, a predetermined amount of the spent acid reacting with the rock disk in the first reactor; and acquiring, by the data acquisition device, temperature and pressure data of the first reactor and the second reactor and controlling, by the data acquisition device, the first reactor and the second reactor based on the acquired temperature and pressure data of the first reactor and the second reactor, wherein the rock disk is reacted with the spent acid in the first reactor under a first reservoir condition comprising a first high temperature and a second high pressure, wherein the spent acid is produced by reacting the rock with the acid aqueous solution in the second reactor under a second reservoir condition comprising a second high temperature and a second high pressure, wherein the first reactor comprises a first reaction vessel in which the rock disk reacts with the spent acid, a first heating jacket, a first magnetic drive, and a first sensor, wherein the method further comprises:

maintaining, by the first heating jacket, the temperature of the first reservoir condition in the first reaction vessel;

measuring, by first sensor, an internal temperature and a pressure of the first reaction vessel; and rotating, by the first magnetic drive, a shaft connected to the rock disk at a first rotating speed when the rock disk reacts with the spent acid, wherein the second reactor comprises a second reaction vessel in which the rock reacts with the acid aqueous solution, a second heating jacket, a second magnetic drive, a second sensor and a cylinder, the second reaction vessel including a permeable container containing the rock, wherein the method further comprises:

maintaining, by the second heating jacket, the temperature of the second reservoir condition in the second reaction vessel;

rotating, by the second magnetic drive, a shaft connected to the permeable container containing the rock at a second rotating speed when the rock reacts with the acid aqueous solution;

measuring, by the second sensor, an internal temperature and a pressure of the second reaction vessel; and introducing, by the cylinder, the spent acid stored in the second reaction vessel into the first reactor by pushing the spent acid to the outside of the second reaction vessel, wherein the temperature and pressure data of the first reactor and the second reactor are acquired by the data acquisition device from the first sensor and the second sensor, and temperatures of the first reaction vessel and the second reaction vessel are adjusted by the data acquisition device by controlling the first heating jacket and the second heating jacket, and wherein the first rotating speed of the first magnetic drive and the second rotating speed of the second magnetic drive are adjusted by the data acquisition device based on the acquired temperature and pressure data of the first reactor and the second reactor.

8. The method of claim 7, wherein the sample extractor comprises a first sampling valve, a sampling line connected to the first sampling valve, a second sampling valve connected to the sampling line and a sampling tank connected to the second sampling valve, wherein the method further comprises moving, by the first sampling valve, the acid reacting with the rock disk in the first reactor to the sampling line and moving, by the second reaction valve, the acid loaded in the sampling line to the sampling tank and storing the acid from sampling line in the sampling tank.

9. The method of claim 7, wherein the apparatus further comprises a vent connected to the first reactor and the second reactor, and wherein the method further comprises discharging, by the vent, internal fluid of the first reactor to the outside after the reaction of the rock disk with the acid finishes in the first reactor and discharging, by the vent, internal fluid of the second reactor to the outside after the reaction of the rock with the acid aqueous solution finishes in the second reactor.

10. The method of claim 9, wherein the vent comprises a neutralization tank configured to load a neutralizing agent therein to neutralize an acid, a first vent valve and a second vent valve, wherein the method further comprises moving, by the first vent valve, the internal fluid of the first reactor to the neutralization tank after the reaction of the rock disk with the acid finishes, and moving, by the second vent valve, the internal fluid of the second reactor to the neutralization tank after the reaction of the rock with the acid aqueous solution finishes.

11. The method of claim 7, further comprising calculating a dissolution rate and a diffusion coefficient of the acid reacting with the rock through the first reactor and the second reactor by using the acid extracted by the sample extractor.

\* \* \* \* \*